United States Patent [19]

Burgin

[11] 4,300,541
[45] Nov. 17, 1981

[54] SPECULUM LENS STRUCTURE

[76] Inventor: Kermit Burgin, R.R. 1, Box 334, Whitestown, Ind. 46075

[21] Appl. No.: 180,352

[22] Filed: Aug. 22, 1980

Related U.S. Application Data

[63] Continuation of Ser. No. 10,751, Feb. 9, 1979, abandoned.

[51] Int. Cl.³ .............................................. A61B 1/06
[52] U.S. Cl. ..................................................... 128/18
[58] Field of Search ..................... 128/3, 4, 5, 6, 9–13, 128/15–18, 20–23, 341, 345, 242, 244, 397, 398

[56] References Cited

U.S. PATENT DOCUMENTS

| | | | |
|---|---|---|---|
| 471,990 | 3/1892 | Daily | 128/18 |
| 559,122 | 4/1896 | Daily | 128/18 |
| 605,652 | 6/1898 | Pitt | 128/18 |
| 872,343 | 12/1907 | Griswold | 128/18 |
| 872,344 | 12/1907 | Griswold | 128/18 |
| 1,094,575 | 4/1914 | Joutras | 128/18 |
| 1,222,478 | 4/1917 | Sheaff | 128/18 |
| 1,706,500 | 3/1929 | Smith | 128/20 |
| 2,247,258 | 6/1941 | Shepard | 128/16 |
| 2,482,971 | 9/1949 | Golson | 128/6 |
| 2,690,745 | 10/1954 | Govan | 128/15 |
| 3,131,690 | 5/1964 | Innis et al. | 128/23 |
| 3,324,850 | 6/1967 | Gunning et al. | 128/18 |
| 3,532,088 | 10/1970 | Fiore | 128/18 |
| 3,592,199 | 7/1971 | Ostensen | 128/6 |
| 3,664,330 | 5/1972 | Deutsch | 128/18 |
| 3,716,047 | 2/1973 | Moore et al. | 128/18 |
| 3,744,481 | 7/1973 | McDonald | 128/17 |
| 3,762,400 | 10/1973 | McDonald | 128/18 |
| 3,789,835 | 2/1974 | Whitman | 128/18 |
| 3,796,214 | 3/1974 | Davis | 128/20 |
| 3,851,642 | 12/1974 | McDonald | 128/18 |
| 4,086,919 | 5/1978 | Bullard | 128/6 X |

FOREIGN PATENT DOCUMENTS

| | | | |
|---|---|---|---|
| 2302614 | 7/1974 | Fed. Rep. of Germany | 128/15 |
| 273809 | 4/1948 | Switzerland | 128/18 |
| 25040 | of 1912 | United Kingdom | 128/24 |

*Primary Examiner*—John D. Yasko
*Attorney, Agent, or Firm*—Jenkins, Coffey, Hyland, Badger & Conard

[57] ABSTRACT

A disposable contacting member molded from an optical wave-guiding material includes a socket adapted to hold a light source and a lens for directing light from the source into an orifice or incision. The lens is on the inner side wall of the contacting member, facing away from the wall of the orifice or incision. The lens is of a sufficiently low profile that is does not obstruct access to the orifice or incision.

21 Claims, 11 Drawing Figures

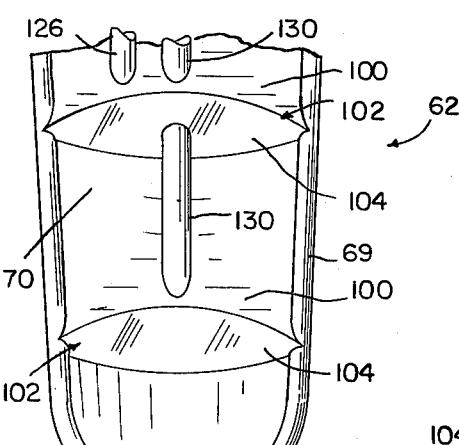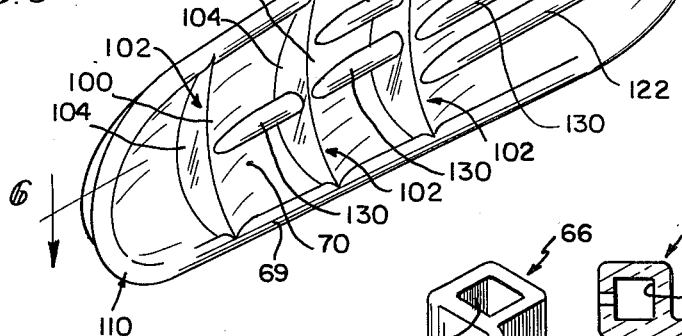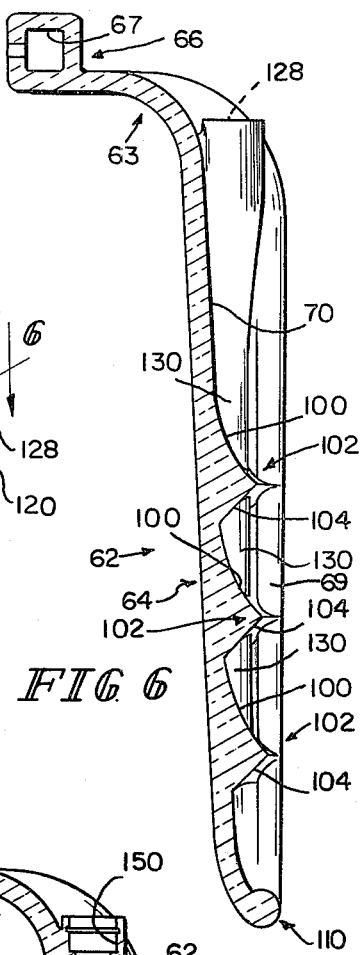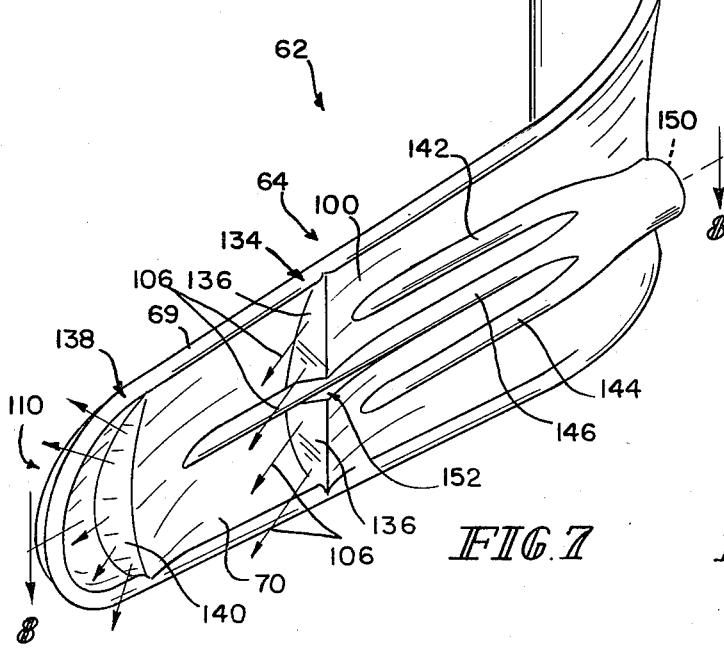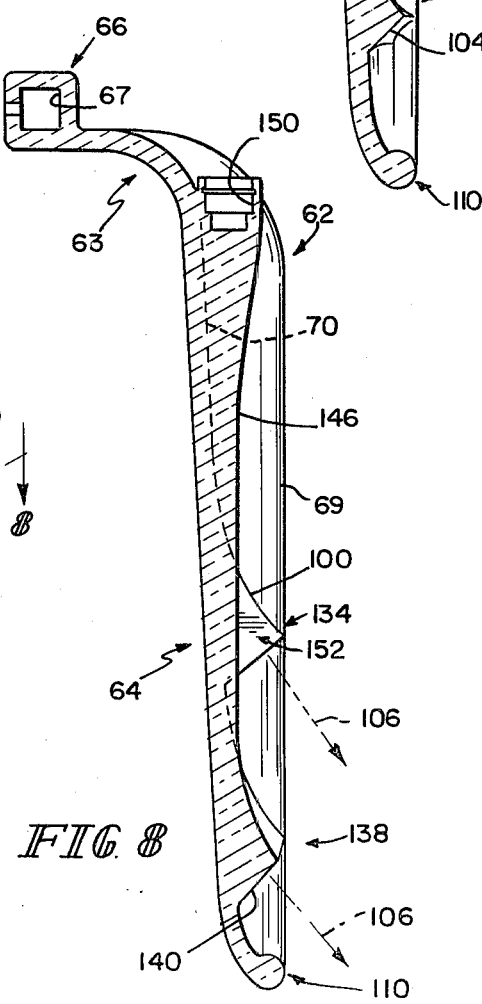

SPECULUM LENS STRUCTURE

This is a continuation of application Ser. No. 10,751 filed Feb. 9, 1979, now abandoned.

This invention relates generally to apparatus for dilating orifices and incisions, and specifically to a new structure for the blades or contacting members of such apparatus.

There are many known types of specula, forceps and the like for enlarging body orifices or incisions for such purposes as examination or surgery. Some of these specula and forceps include light sources intended to provide light in the orifice or incision to assist an examiner or surgeon. For the most part, however, these well-known devices require sterilization between uses; are not adaptable for use in orifices and incisions having different sizes, shapes, depths and so forth; and are provided with light sources so situated that the ability of the user to examine, or operate in, an orifice or incision is at least partially obstructed. See, for example, the following U.S. Patents:

| U.S. PAT. NO. | INVENTOR | ISSUE DATE |
| --- | --- | --- |
| 1,706,500 | Smith | March 26, 1929 |
| 1,222,478 | Sheaff | April 10, 1917 |
| 605,652 | Pitt | June 14, 1898 |
| 1,094,575 | Joutras | April 28, 1914 |
| 3,716,047 | Moore et al | Feb. 13, 1973 |

In my copending applications Ser. No. 811,550, filed June 30, 1977, Ser. No. 958,795, filed Nov. 8, 1978 both entitled Plastic Forceps, Ser. No. 901,521, filed May 1, 1978 and Ser. No. 958,794, filed Nov. 8, 1978, both entitled Locking Adjustable Speculum, I have disclosed solutions to some of the aforementioned problems associated with prior art specula and forceps. This application is related to those applications. It is believed that the improved contacting member for speculum or forceps provided by the present invention offers solutions to all of the problems mentioned above by incorporating features including a fiber optic or optical wave-guiding means extending between a light source in a portion of the contacting member remote from the orifice or incision and a lens located on the wall of the contacting member at the orifice or incision. The lens directs light provided through the optical wave-guiding means from the source into the orifice or incision.

According to the invention, a contacting member for a speculum or forceps includes a portion for attachment to the speculum or forceps and a portion for insertion into an orifice or incision. The portion for insertion is elongated and has a side facing away from the wall of the incision, a smooth generally convex side for contacting the wall of the incision and an edge separating the two sides and extending around a portion of the perimeter of the contacting member. Means are provided, either on the contacting member itself or on associated speculum components, for mounting a light source on the speculum remote from the incision. The remote mounting of the light source generally keeps it from contact with the orifice or incision. Sterilization requirements for the light source will thereby be made substantially easier to meet. A lens is disposed on the side of the contacting member facing away from the wall of the incision or orifice. The contacting member further includes means for transmitting light from the source of the lens. The lens directs the light onto the orifice or incision to illuminate the incision.

Illustratively, the means for transmitting light from the source of the lens comprises an optical wave-guiding rib in the contacting member. Suitable materials having optical wave-guiding properties to perform this function include polymethylacrylate.

In the illustrative embodiments, the sides of the contacting members facing away from the wall of the orifice or incision are generally concave in transverse section. The means for mounting the light source on the speculum includes means for attaching the light source either to the contacting member itself, or to a portion of the speculum adjacent the contacting member. In the latter instance, means must be provided for transmitting light from the speculum portion into the contacting member. An illustrative attachment means includes a socket for connecting a lamp bulb to the contacting member itself.

A contacting member for a medical instrument includes means cooperating with the medical instrument to mount the contacting member on the medical instrument and means projecting away from the mounting means to contact a meatus. Means are provided for mounting a light source remote from the meatus, and for transmitting light along the contacting member away from the mounting means. A lens is formed on the contacting member for directing the transmitted light in a desired manner into the meatus. The lens is formed at the end of the transmitting means remote from the source, and includes a surface for directing light into the meatus, the surface causing diffusion or spreading of the light as it passes through the surface into the meatus. Alternatively the surface is formed to cause focussing of the light.

The invention may best be understood by referring to the following description and accompanying drawings which illustrate the invention. In the drawings:

FIG. 4 is a perspective view of another contacting member constructed according to the present invention;

FIG. 5 is a detail of the end of the contacting member illustrated in FIG. 4;

FIG. 6 is a sectional view of the contacting member of FIG. 4, taken generally along section lines 6—6 of FIG. 4;

FIG. 7 is a perspective view of another contacting member constructed according to the present invention;

FIG. 8 is a sectional view of the contacting member of FIG. 7, taken generally along section lines 8—8 of FIG. 7;

Figure 9:
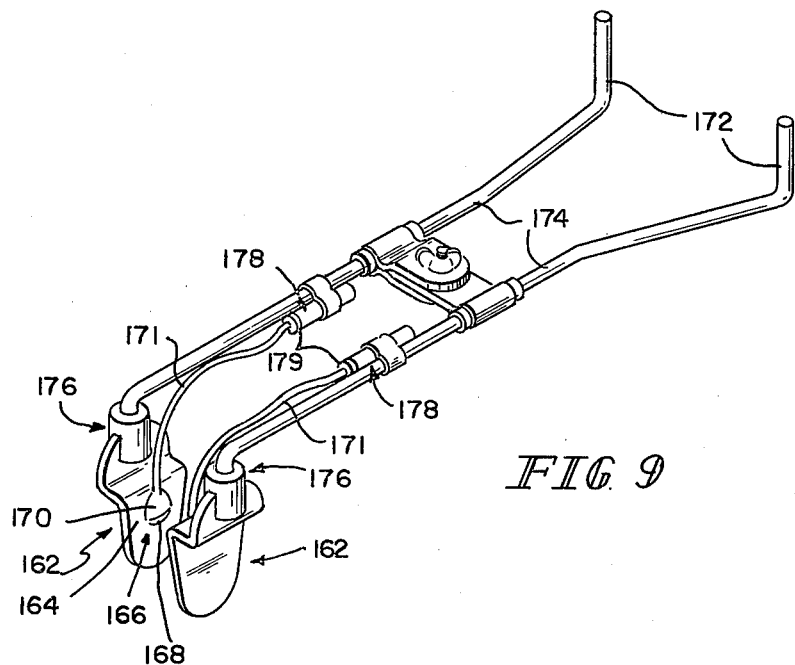
Figure 10:
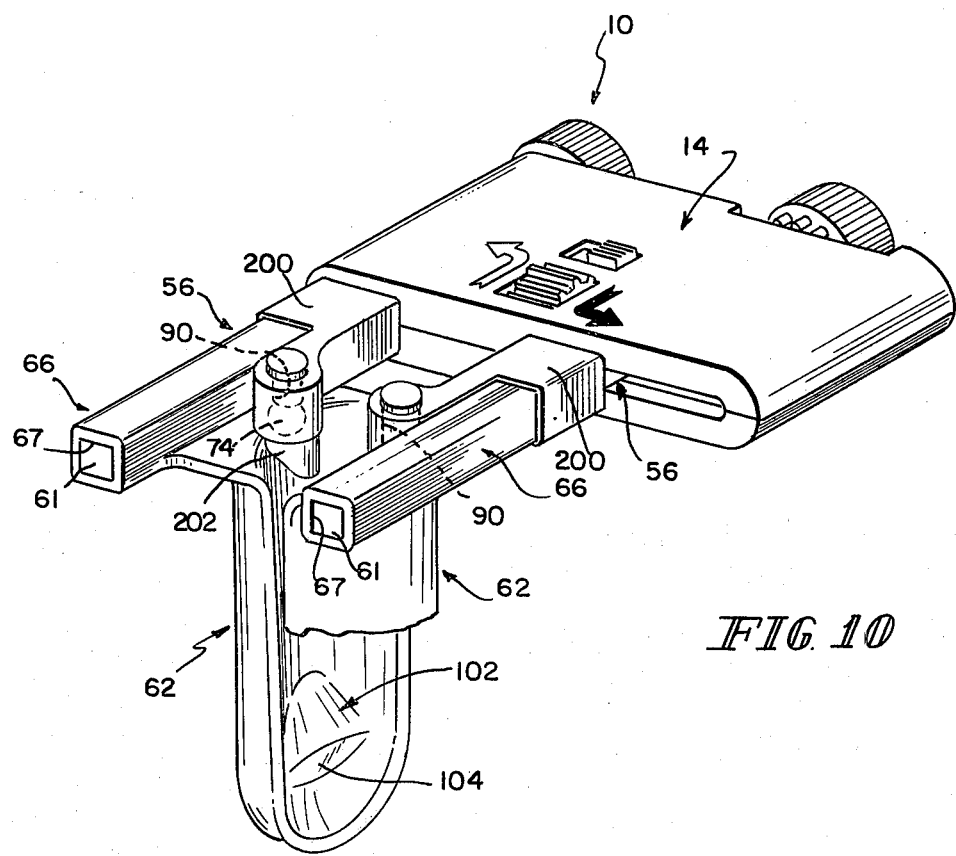
Figure 11:
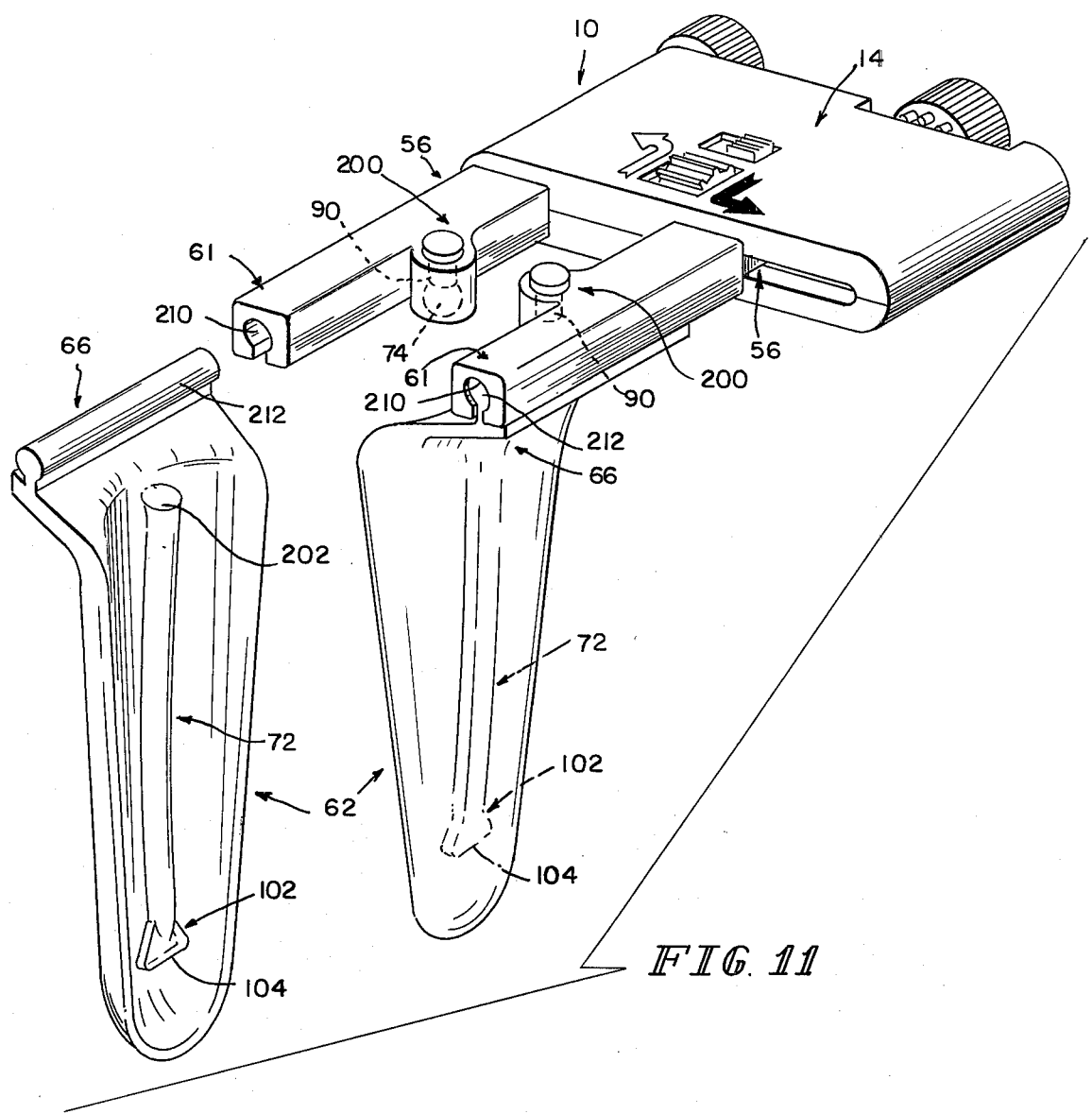

FIG. 9 is a perspective view of forceps of the type described in my co-pending applications Ser. Nos. 811,550 and 958,795, with contacting members constructed according to the present invention; and FIGS. 10–11 are perspective views of specula of the type described in my co-pending application Ser. No. 958,794, with contacting members constructed according to the present invention.

Figure 1:
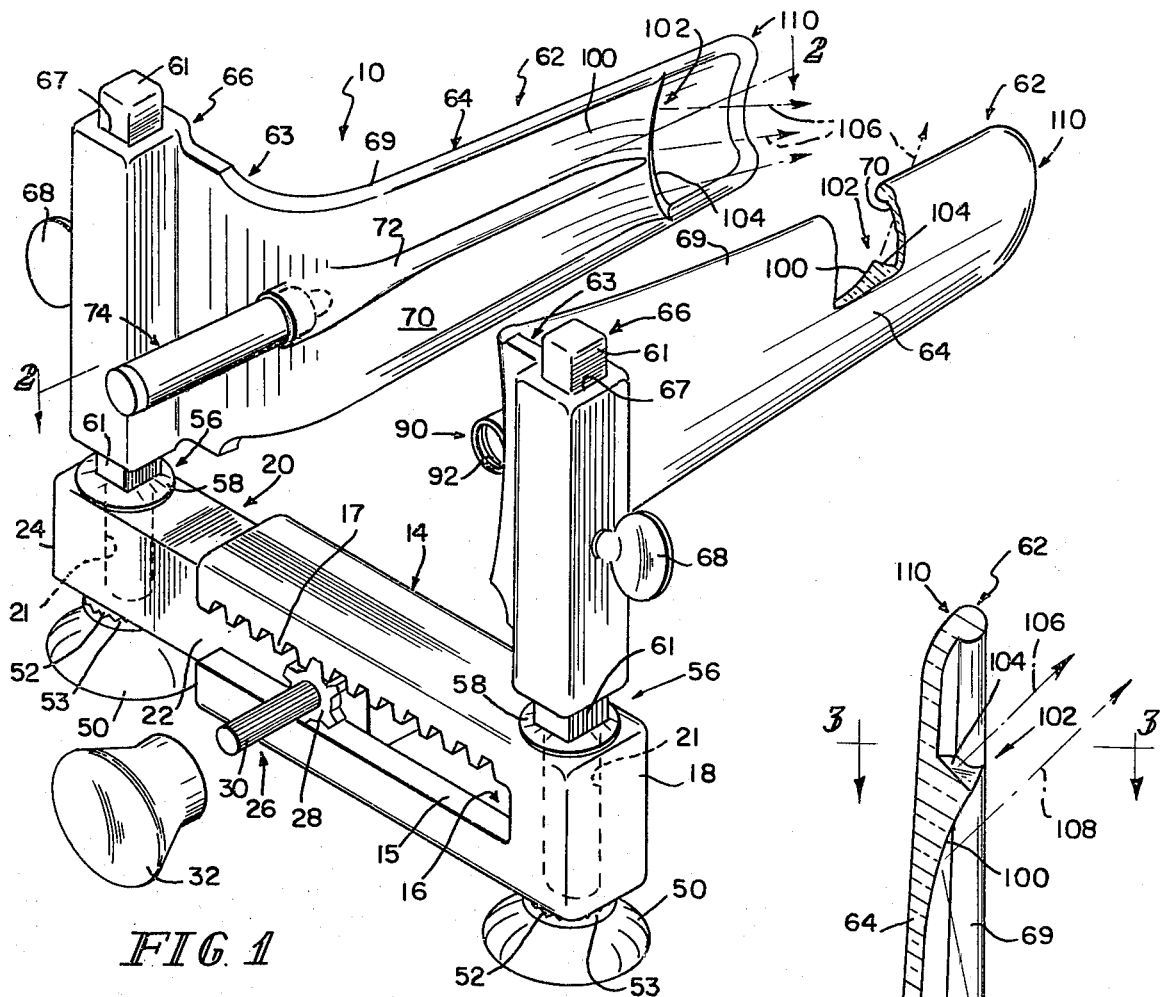
FIG. 1 is a perspective view of an apparatus provided with contacting members constructed according to the present invention.

Referring particularly to FIG. 1, a speculum 10 includes a base 12 having first and second members 14 and 20, respectively, adjustably coupled to each other. First member 14 includes a hollow interior 16. A slot 15 is formed in first member 14 as shown, with a series of gear teeth 17 situated along a surface of the slot 15. Second member 20 includes a portion 22 longitudinally movably received within the interior 16 of the first member 14. As illustrated in FIG. 1, a crown gear-like ring 52 has been provided on the underside of each of base members 14, 20. The rings 52 may be attached to the base members 14 and 20 by any suitable means or may be formed with the base members 14 and 20 themselves.

The base 12 further includes means 26 rotatably coupled to portion 22 of base member 20 for incrementally adjusting the distance between the distal portions 18 and 24 of the base members 14 and 20, respectively. Incremental adjusting means 26 includes a spur gear 28 fixed to a rotatable shaft 30. A knob 32 is attached to shaft 30 for rotation by the speculum operator to rotate gear 28. The spur gear 28 includes a plurality of teeth which engage teeth 17 situated along the surface of slot 15 in base member 14. When the speculum operator rotates the knob 32, the distal portions 18 and 24 of the base members 14 and 20, respectively, are adjusted to a desired separation. The spur gear 28 can be formed separately from the knob 32, as illustrated, or can be formed on the knob. Additional specific details of construction and operation of the speculum illustrated in FIG. 1 are described in considerable detail in my aforementioned copending U.S. patent applications Ser. Nos. 901,521 and 958,794. Such description is incorporated herein by reference for those details.

Speculum 10 further includes two elongated shafts 56 which are rotatably mounted in distal portions 18 and 24 of base members 14, 20, respectively. The shafts 56 extend through apertures 21 located in the distal portions 18 and 24 and into knobs 50. Knobs 50 have crown gear teeth 53 provided in their surfaces adjacent the rings 52. Engagement of teeth 53 with respective rings 52 prevents the shafts 56 from rotating in members 14, 20 from selected rotational positions.

Two members 62 are provided for dilating or enlarging an incision, orifice, or meatus. Each member 62 has a portion 64 for contacting and restraining a wall portion of the orifice or incision and a proximal end 66 detachably engaging a portion of the elongated rotatable shaft 56. Each member 62 has a generally convex exterior surface for contacting the wall of the incision or orifice. Each member 62 also includes a shoulder 63 adjacent its proximal end 66. Shoulders 63 rest against external body surfaces to support the speculum 10 away from the external body surfaces and prevent, to the greatest possible extent, contamination of the speculum members 14, 20, 56 by organisms on such external surfaces. The edges 69 of the members 62 are beaded, or rounded, to minimize the likelihood of tissue damage from edges 69. The elongated rotatable shafts 56 are engaged in sockets 67 provided on the proximal ends 66 of members 62 to mount the members 62 on the distal portions 18 and 24 of base members 14 and 20, respectively. The portions of rotatable shafts 56 which are engaged in sockets 67 include rectangular portions 61 for preventing members 62 from rotating with respect to shafts 56. Rectangular portions 61 extend through the sockets 67 in the proximal ends 66 of members 62. Spring washers 58 are interposed between the rectangular portions 61 of shafts 56 and the respective base members 14 and 20 to urge rectangular portions 61 away from members 14, 20 and teeth 53 into engagement with rings 52.

Thumbscrews 68 are threaded into apertures located in the proximal ends 66 of members 62. By advancing thumbscrews 68, the extended rectangular portions of shafts 56 are engaged, fixing the positions of the members 62 along the shafts 56. It should be noted that members 62 may be independently rotatably adjusted through various angles and sustained at various positions along their respective shafts 56 independently of each other, permitting the speculum operator the flexibility to adjust the speculum 10 to accommodate various types and shapes of orifices.

Each member 62 is elongated and has a concave inner surface 70. An elongated rib 72 is disposed on each concave inner surface 70. Illustratively, rib 72 has a generally circular or semicircular transverse section. Light from an external light source 74 is directed along the rib 72, which in the illustrated embodiment is a molded rib of optical wave-guiding material such as polymethylmethacrylate (LUCITE or PLEXIGLAS). The light is transmitted down the concave inner surfaces 70 of member 62 directly into the orifice or incision. Since members 62 are detachable from the shafts 56, various other shapes and sizes of members 62 may be used with the speculum 10 depending upon the size, shape or depth of the orifice or incision to be dilated.

A socket 90 is provided adjacent the shoulder 63 of each contacting member 62. Each socket 90 includes a locking groove 92 receiving a split locking ring 94 (FIG. 2) on the light source 74 to hold the light source 74 securely in the socket 90.

Figures 2, 3:
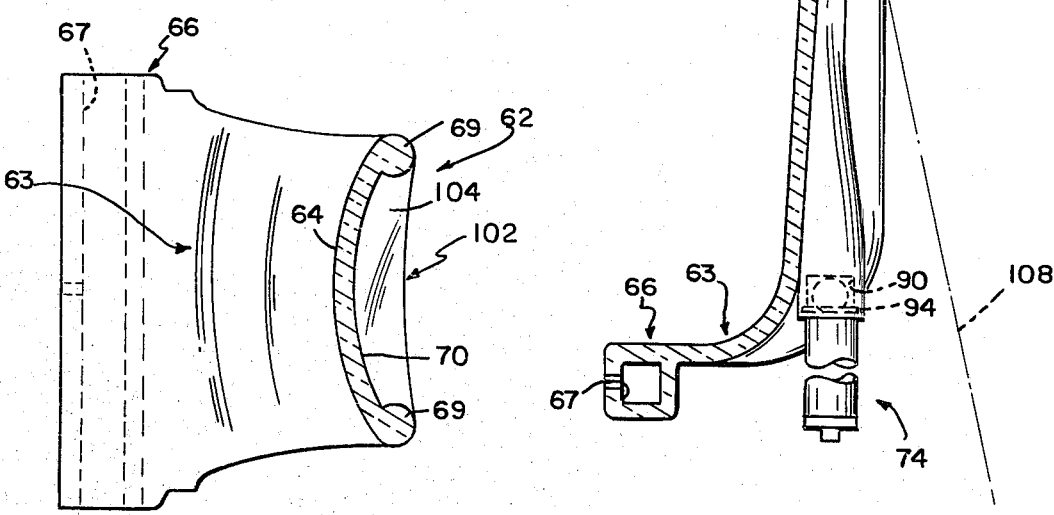
FIG. 2 is a sectional view of one of the contacting members illustrated in FIG. 1, taken generally along section lines 2—2 of FIG. 1.
FIG. 3 is a sectional view of a contacting member of FIG. 2, taken generally along section lines 3—3 of FIG. 2.

Each wave-guiding rib 72 terminates at a gradually inwardly and forwardly sloping, transversely extending surface 100 of a lens 102. As best illustrated in FIGS. 1, 3, each lens 102 extends transversely across its contacting member 62 between the beads of the opposite edges 69. A somewhat more sharply sloping surface 104 of each lens 102 directs the light provided through its respective rib 72 forwardly and inwardly into the incision as indicated by the arrows 106 in FIGS. 1-2. In addition, the gradually sloping surface 100 is also useful to reflect light downward into the incision, as indicated by arrow 108 in FIG. 2. As best illustrated in FIGS. 1-2, the forward surfaces 104 of lenses 102 are somewhat concave. That is, surfaces 104 extend toward the distal ends 110 of contacting members 62 adjacent edges 69, and away from distal ends 110 of contacting members 62 at the transverse centers of the contacting members 62. This configuration provides some convergence or focusing of the light rays, illustrated by arrows 106 in FIG. 1.

In the remaining illustrated embodiments of the invention, those elements having the same reference numerals as in the embodiments of FIGS. 1-3 perform the same or similar functions.

In the embodiment of FIGS. 4-6, three lenses 102 are spaced apart longitudinally along the contacting member 62. Although these lenses are spaced apart equidistantly along the length of contacting members 62, different spacings between adjacent lenses 102 can be used to achieve a particular distribution of light in the orifice or incision, as required.

The lens 102 most remote from the distal end 110 of contacting member 62 is provided with light from a source (not shown) insertable into a socket 120. The light from socket 120 travels through a lower optical wave-guiding rib 122 which supplies the light for the rearward lens 102. An upper socket 124, adapted to receive a light source (not shown), supplies light through an optical wave-guiding rib 126. Rib 126 extends through the rearward and forward surfaces 100, 104, respectively, of the rearward lens 102 and supplies light to the middle lens 102. A centrally disposed socket 128 is adapted to engage a third light source (not shown). Light from the source at socket 128 is supplied through an optical wave-guiding rib 130 which extends through the rearward and forward surfaces 100, 104 of both the rearward and middle lenses 102 to supply light to the forward lens 102 adjacent the distal end 110 of contacting members 62.

In the embodiment of FIGS. 7–8, a rearward lens 134 is provided with a flat forward lens surface 136, as best illustrated in FIG. 7. Light is directed in substantially parallel rays 106 from surface 136 into the orifice or incision. The forward lens 138 of this contacting member 62 has a convex forward surface 140. Convex surface 140 provides diverging rays 106, as best illustrated in FIG. 7.

Light for lenses 134, 138 is supplied through a trifurcated rib arrangement including optical wave-guiding ribs 142, 144, 146. All of ribs 142, 144, 146 extend forward from a single light source (not shown) retaining socket 150. The use of a single source in socket 150 can be more convenient than the use of multiple sources as in sockets 120, 124, 128 of the embodiment of FIGS. 4–6. However, it should be noted that independent control of the light sources in sockets 120, 124, 128 is sacrificed when a single source is used.

Lens 134 is split at 152, at its transverse center to permit optical wave-guiding rib 146 to pass through it between socket 150 and the forward lens 138.

It should be noted that several significant results are achieved with contacting member structures of the type described. First, previously non-functional surfaces of the contacting members 62 have been converted into functional surfaces. For example, the surfaces 100 of the various lenses are so molded as to reflect ambient light downward into the orifice or incision. Further, the lenses 102, 134, 138 of the various embodiments are provided to illuminate selected portions of the orifice or incision being examined. This flexibility in the placement of light in the orifice or incision is enhanced by the availability of concave, flat, or convex surfaces on the lens.

Further, as can best be appreciated from FIGS. 2, 6 and 8, the wall thickness of the contacting members 62 in areas other than the lens areas and rib areas can be made somewhat thinner, so that substantially the same amount of material is required for each contacting member as in the contacting members of my applications Ser. Nos. 901,521 and 958,794. The optical wave-guiding ribs in this sense serve as longitudinal strengthening and stiffening members for the contacting members 62. Similarly, the lenses themselves serve as transverse reinforcing and stiffening members for the contacting members 62.

All of these advantageous results are achieved without significantly raising the inner wall 70 contours of the contacting members 62. That is, these results are achieved without increasing the inner wall contours beyond the boundaries of edges 69. This means that the advantageous results are achieved without forming any protrusions which might otherwise interfere with examination or surgical procedures conducted in the orifice or incision.

It must be appreciated that contacting members having various sizes and shapes as required by the specific needs of a particular examination, surgical procedure or shape of orifice or incision may benefit from the described lens structure. For example, it is not necessary that the outer contours of the contacting member be generally convex, nor that the inner contours of such contacting members be generally concave. The lens structures of the instant invention may be provided on otherwise flat surfaces of contacting members. An example of such a structure is the contacting member 62 illustrated in FIG. 9. This contacting member, and the plastic forceps to which it is attached, are of the same general type described in my aforementioned copending applications Ser. Nos. 811,550 and 958,795, and the descriptions contained in those applications are incorporated herein by reference for the details of those structures.

The contacting members 162 of the embodiment of FIG. 9 have generally flat surfaces 164 provided with lenses 166. Lenses 166 have generally convex forward surfaces 168 and more gently sloping rearward surfaces 170. Flexible fiber optic bundles 171 extend from surfaces 170 upwardly and rearwardly toward the handle 172 ends of the forceps arms 174. The use of flexible fiber optic bundles permits unhindered pivotal action between the contacting members 162 and the distal ends 176 of forceps arms 174, as described in my applications Ser. Nos. 811,550 and 958,795. A light source 178 is mounted on each of arms 174 remote from its distal end 176. Each source 178 is coupled by a socket 179 formed in the remote end of a respective fiber optic bundle 171 to its respective lens 166.

In the apparatus illustrated in FIGS. 10–11, those elements performing the same or similar functions as the corresponding elements of the embodiment of FIG. 1, are numbered similarly. In the embodiment of FIG. 10, one contacting member 62 is shown fragmentarily for purposes of clarity. In FIG. 11, one contacting member 62 is removed from the speculum 10 for purposes of clarity.

In these embodiments, the first member 14 is constructed from, for example, moldable plastic material. Member 14 is constructed in the form of a case having a hollow interior within which the member 20 (not shown) slides. The adjustment mechanism by which the distance between the shafts 56 supported rotatably in members 14, 20 is adjusted is as described in my application Ser. No. 958,794.

The shafts 56 are provided with permanently mounted portions 200 including sockets 90 adapted to hold securely the light sources 74. The portions 200 of the shafts 56 providing the sockets 90 are substantially permanently secured to the shafts 56. Illustratively, shaft portions 200 are constructed from a high-impact moldable plastic. In the embodiment of FIG. 10, the portions 61 of the shafts 56 upon which the members 62 are mounted, are rectangular. These portions 61 cooperate with the rectangular sockets 67 in the proximal ends 66 of members 62. In this embodiment, the inner side walls of the sockets 67 tightly cooperate with the shaft 56 ends 61. The thumb screws 68 of the embodiment illustrated in FIG. 1 are thereby avoided. In the embodiment of FIG. 10, the light from each source 74 is conducted through a built-up pedestal-like portion 202 of each contacting member 62. The contacting members 62 are molded from a transparent optical wave-guiding medium. The ribs 72 of the embodiments of FIGS. 1–8 are avoided, except to the extent required to produce the portions 202. The material from which the contacting members 62 are molded is so molded that a significant portion of the light entering through the portions 202 is transmitted to, and through the surfaces 104 of the lenses 102 of contacting members 62.

In the embodiment illustrated in FIG. 11, the distal ends 61 of shafts 56 are provided with longitudinally extending somewhat "keyhole" shaped cross-section passageways 210. The proximal end 66 of each member 62 is provided with a keyhole-shaped transverse section projection 212 which engages the slot in the distal end 61 of a respective shaft 56.

Each contacting member 62 is provided with a longitudinally extending optical wave-guiding rib 72 terminating at a lens 102 provided with a surface 104 for directing light guided along the rib 72 into the orifice or incision. The light is introduced into the ribs 72 at the somewhat circular or elliptical cross-section rearward ends 202 of the ribs 72. These circular cross-sectional rearward ends 202 are disposed closely adjacent the light sources 74 in respective sockets 90 of shaft portions 200 when the contacting members 62 are in place on the shafts 56.

What is claimed is:

1. In combination, a pair of contacting members and an operating handle for movably mounting the contacting members relative to each other, each contacting member including means cooperating with the operating handle to mount the contacting member on the operating handle, means projecting away from the mounting means to contact a meatus, means for mounting a light source remote from the meatus, means for transmitting light along the contacting member away from the mounting means, and a lens formed on the contacting member for directing the transmitted light in a desired manner into the meatus, the lens being formed at the end of the transmitting means remote from the source, and including a surface for directing light into the meatus, the surface causing diffusion or spreading of the light as it passes through the surface into the meatus.

2. The apparatus of claim 1 in which the light-source mounting means includes means provided on the operating handle, and the transmitting means includes means for engaging the light source to receive light, and means extending from the engaging means to the contacting member for transmitting light from the engaging means to the contacting member.

3. The apparatus of claim 2 in which the means for mounting the contacting member on the operating handle includes means for flexibly mounting the contacting member on the operating handle, and the means for transmitting light from the engaging means to the contacting member is flexible to permit movement of the contacting member relative to the operating handle.

4. The apparatus of claim 3 in which the light-source mounting means includes means for engaging the light source formed on the contacting member remote from the means for contacting the meatus.

5. In combination, a pair of contacting members and an operating handle for movably mounting the contacting members relative to each other, each contacting member including means cooperating with the operating handle to mount the contacting member on the operating handle, means projecting away from the mounting means to contact a meatus, means for mounting a light source remote from the meatus, means for transmitting light along the contacting member away from the mounting means, and a lens formed on the contacting member for directing the transmitted light in a desired manner into the meatus, the lens being formed at the end of the transmitting means remote from the source, and including a surface for directing light into the meatus, the surface causing focussing of the light as it passes through the surface into the meatus.

6. The apparatus of claim 5 in which the light-source mounting means includes means provided on the operating handle, and the transmitting means includes means for engaging the light source to receive light, and means for transmitting light from the engaging means to the contacting member extending from the engaging means to the contacting member.

7. The apparatus of claim 5 in which the means for mounting the contacting member on the operating handle includes means for flexibly mounting the contacting member on the operating handle, and the means for transmitting light from the engaging means to the contacting member is flexible to permit movement of the contacting member relative to the operating handle.

8. The apparatus of claim 5 in which the light-source mounting means includes means for engaging the light source formed on the contacting member remote from the means for contacting the meatus.

9. A medical instrument, comprising a pair of contacting members and an operating handle for movably mounting the contacting members relative to each other, each contacting member including means cooperating with the operating handle to mount the contacting member on the operating handle, means projecting away from the mounting means to contact a meatus, means for mounting a light source remote from the meatus, means for transmitting light along the contacting member away from the mounting means, and a lens formed on the contacting member for directing the transmitted light in a desired manner into the meatus, the lens being formed at the end of the transmitting means remote from the source, and including a surface for directing light into the meatus, the surface causing diffusion or spreading of the light as it passes through the surface into the meatus.

10. A medical instrument, comprising a pair of contacting members and an operating handle for movably mounting the contacting members relative to each other, each contacting member including means cooperating with the operating handle to mount the contacting member on the operating handle, means projecting away from the mounting means to contact a meatus, means for mounting a light source remote from the meatus, means for transmitting light along the contacting member away from the mounting means, and a lens formed on the contacting member for directing the transmitted light in a desired manner into the meatus, the lens being formed at the end of the transmitting means remote from the source, and including a surface for directing light into the meatus, the surface causing focussing of the light as it passes through the surface into the meatus.

11. A medical instrument including a pair of contacting members and an operating handle for movably mounting the contacting members relative to each other, each contacting member including a portion for attachment to the operating handle and a portion for insertion into a meatus, the portion for insertion having a side facing away from the wall of the meatus, a side for contacting the wall of the meatus and an edge separating the two sides and extending around a portion of the perimeter of the contacting member, means for mounting a light source remote from the meatus, a lens formed on the side facing away from the wall of the meatus, and means for transmitting light along the contacting member to the lens, the means for mounting the light source including means for attaching the light source to the contacting member on the side facing away from the meatus wall adjacent the portion for attachment to the speculum.

12. The apparatus of claim 11 wherein the means for transmitting light along the contacting member comprises optical wave-guiding means on the side facing away from the meatus and extending between the attachment means and the lens to transmit light from the source to the lens.

13. The apparatus of claim 11 wherein the attachment means includes a socket for connecting a lamp bulb to the contacting member.

14. The apparatus of claim 12 wherein the side facing away from the meatus wall is generally concave.

15. The apparatus of claim 11 wherein the side for contacting the wall of the meatus is generally convex.

16. The apparatus of claim 11 wherein the edge includes means providing a smooth protective bead.

17. In combination, a contacting member and an operating handle for supporting and manipulating the contacting member in a meatus, the operating handle including a shaft provided with a longitudinally extending slot opening in an end and a side wall thereof, and an enlarged longitudinally extending opening in the interior thereof and opening in said end, the slot intersecting the opening, the contacting member including a portion for attachment to the shaft, the attachment portion including a first part engageable in the slot and a second portion engageable in the enlarged portion.

18. The apparatus of claim 17 wherein the enlarged opening is generally circular in transverse section.

19. In combination, a contacting member and an operating handle for supporting and manipulating the contacting member in a meatus, the operating handle including a shaft provided with a longitudinally extending keyhole-shaped transverse section opening intersecting a side wall of the shaft, and the contacting member including a portion for attachment to the shaft, the attachment portion including a keyhole-shaped projection for sliding insertion into the opening.

20. The apparatus of claim 17 or 19 in which the operating handle includes a pair of such shafts and including two such contacting members.

21. The apparatus of claim 1, 5, 9, 10, 11, 17, or 19 wherein each said contacting member includes a plurality of such lenses arranged to direct light into the meatus in a desired manner.

* * * * *

UNITED STATES PATENT AND TRADEMARK OFFICE
CERTIFICATE OF CORRECTION

PATENT NO. : 4,300,541
DATED : November 17, 1981
INVENTOR(S) : Kermit Burgin

It is certified that error appears in the above-identified patent and that said Letters Patent are hereby corrected as shown below:

In the Abstract, line 7 should read -- sufficiently low profile that it does not obstruct access --.

Column 2, line 1, "onto" should be -- into --.

Column 4, line 49 should read -- tal ends 110 of contacting members 62 adjacent edges 69, --.

Column 5, line 51, "thickness" should be -- thicknesses --.

Column 7, line 22, "cross-sectional" should be -- cross-section --; line 58, "claim 3" should be -- claim 1 --.

Column 8, line 17, "claim 5" should be -- claim 6 --.

Column 9, line 18, "claim 11" should be -- claim 12 --; line 21, "claim 12" should be -- claim 11 --.

Column 10, line 24, should read -- The apparatus of claim 1, 5, 9, 10 or 11 --.

Signed and Sealed this

Twentieth Day of April 1982

[SEAL]

Attest:

GERALD J. MOSSINGHOFF

Attesting Officer    Commissioner of Patents and Trademarks